US006387670B1

(12) United States Patent
Leblois-Prehaud et al.

(10) Patent No.: US 6,387,670 B1
(45) Date of Patent: May 14, 2002

(54) METHOD FOR PRODUCING RECOMBINANT VIRUS

(75) Inventors: Hélène Leblois-Prehaud, Guyancourt; Michel Perricaudet, Ecrosnes; Emmanuelle Vigne, Ivry sur Seine; Patrice Yeh, Gif sur Yvette, all of (FR)

(73) Assignee: Aventis Pharma, S.A., Antony (FR)

( * ) Notice: Subject to any disclaimer, the term of this patent is extended or adjusted under 35 U.S.C. 154(b) by 0 days.

(21) Appl. No.: 09/308,398

(22) PCT Filed: Nov. 18, 1997

(86) PCT No.: PCT/FR97/02073

§ 371 Date: May 18, 1999

§ 102(e) Date: May 18, 1999

(87) PCT Pub. No.: WO98/22607

PCT Pub. Date: May 28, 1998

(30) Foreign Application Priority Data

Nov. 22, 1996 (FR) .............................................. 96 14278

(51) Int. Cl.$^7$ ............................................. C12N 13/00
(52) U.S. Cl. .................. 435/173.3; 424/93.2; 435/69.1; 435/69.8; 435/70.1; 435/235.1; 435/320.1; 435/325; 435/455; 435/456; 435/457; 435/462; 514/44; 536/23.1; 536/23.72; 935/11; 935/32
(58) Field of Search ................................ 435/69.1, 69.8, 435/70.1, 173.3, 235.1, 320.1, 325, 455–457, 462; 514/44; 935/11, 32; 536/23.1, 23.72; 424/93.2

(56) References Cited

U.S. PATENT DOCUMENTS 5,508,186 A * 4/1996 Young et al. ............ 435/235.1

FOREIGN PATENT DOCUMENTS

| WO | WO 96/07734 | 3/1996 |
| WO | WO 96/09074 | 3/1996 |

OTHER PUBLICATIONS

Yamshchikov et al. Assembly of SIV virus–like particles containing envelpoe proteins using a baculovirus expression sytem. Virology (1995) vol. 214, pp. 50–58.*

Lochmuller et al. Emergence of early region 1–containing replication–competent adenovirus in stocks of replication–defective adenovirus recombinants (E1+E3) during mutliple passages in 293 cells. Human Gene Therapy (1994) vol. 5, pp. 1485–1491.*

McCarty et al. Identification of linear DNA sequences that specifically bind the adeno–associated virus Rep protein. Journal of Virology. (1994) vol. 68, No. 8, pp. 4988–4997.*

Peeper et al. Expression, purification, and functional chracterization of adenovirus 5 and 12 E1a proteins produced in insect cells. Virology (1992) vol. 190, No. 2, pp. 733–745.*

Boyce et al. Baculovirus–mediated gene transfer into mamalian cells. Proceedings of the National Academy of Sciences. vol. 93 (1996) pp. 2348–2352.*

Hofman et al. Efficient gene transfer into human hepatocytes by baculovirus vectors. Proceedings of the National Academy of Sciences. vol. 92 (1995) pp. 10099–10103.*

Possee R.D., "Baculoviruses as expression vectors." Current Opinion in Biotechnology vol. 8 (1997), p. 569–572.*

Peakman et al., Highly efficient generation of recombinant baculoviruses by enzymatically mediated site–specific in vitro recombination, Nucleic Acids Research, 20(3), 495–500 (1992).

Karayan et al., Oligomerization of Recombinant Penton Base of Adenovirus Type 2 and Its Assembly with Fiber in Baculovirus–Infected Cells, Virology 202, 782–795 (1994).

Abstract P 62, "A baculovirus–based method to produce recombinant adeno–associated virus vectors." K. Sollerbrant et al., *The Journal of Gene Medicine*, Oct. 2000, 8th Meeting of the ESGT/Viral Gene Therapy Vectors.

"Efficient gene transfer into various mammalian cells, including non–hepatic cells, by baculovirus vectors." I. Shoji et al., *Journal of General Virology*, 1997, 78, 2657–2664.

"Efficient transduction of neural cells in vitro and in vivo by a baculovirus–derived vector." C. Sarkis et al., *PNAS*, Dec. 19, 2000, vol. 97, No. 26.

"Baculovirus–Mediated Expression of Bacterial Genes in Dipteran and Mammalian Cells." L. Carbonell et al., *Journal of Virology*, Oct. 1985, p. 153–160.

* cited by examiner

*Primary Examiner*—Jeffrey Stucker
*Assistant Examiner*—Ulrike Winkler
(74) *Attorney, Agent, or Firm*—Wiley Rein & Fielding LLP

(57) ABSTRACT

The invention concerns a method for producing recombinant virus. This method is based on the use of baculovirus for providing the complementary functions. It also concerns constructs used for implementing this method, the producing cells, and the resulting virus.

27 Claims, 5 Drawing Sheets

METHOD FOR PRODUCING RECOMBINANT VIRUS

Figure 1:
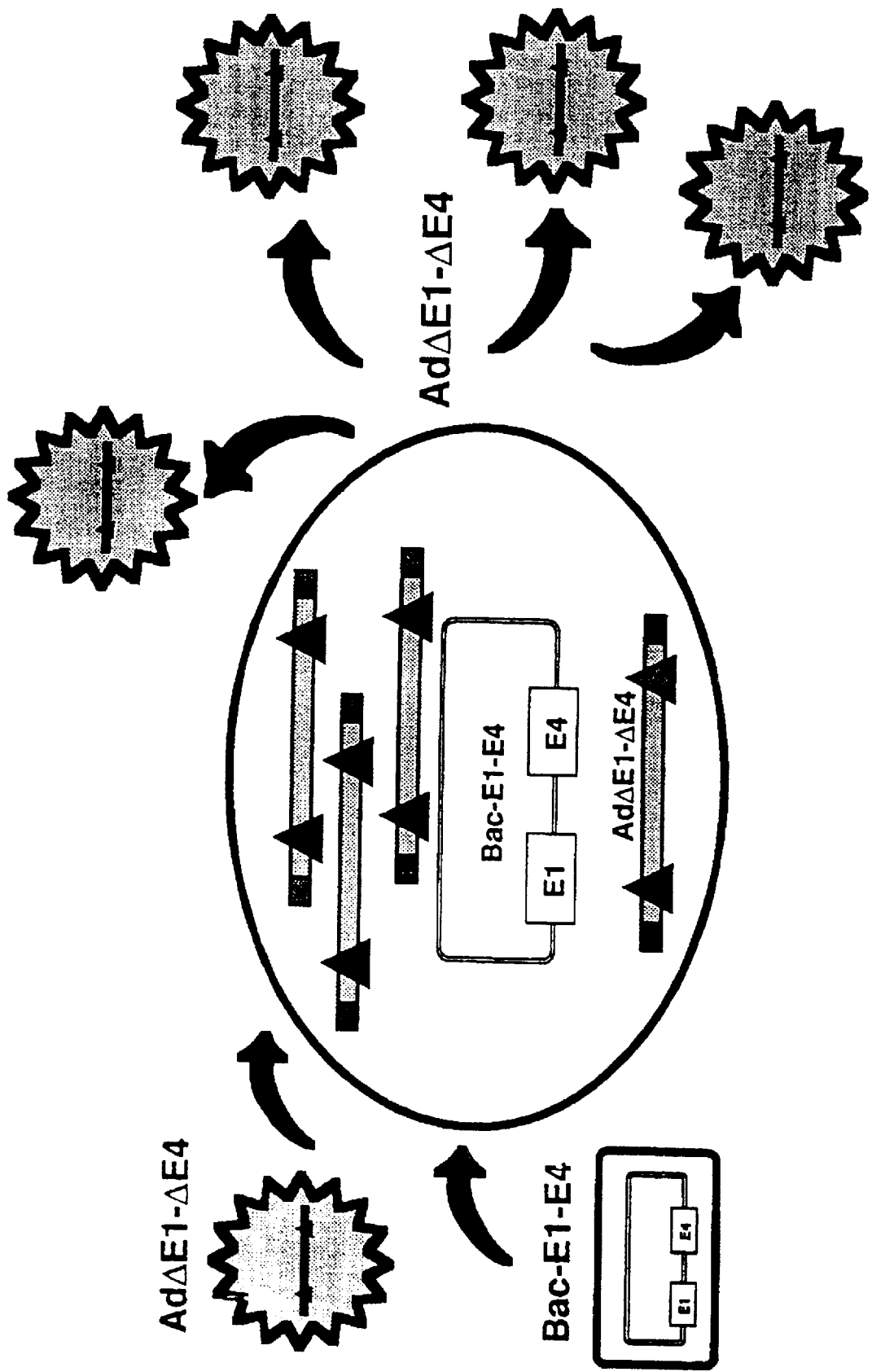

This application is the U.S. national phase under U.S.C. §371 of international application No. PCT/FR97/02073, filed on Nov. 18, 1997.

The present invention relates to a method for the production of recombinant viruses. It also relates to constructs used for carrying out this method, the producing cells, and the viruses thus produced. These viruses can be used as vector for the cloning and/or expression of genes in vitro, ex vivo or in vivo.

Vectors of viral origin are widely used for the cloning, transfer and expression of genes in vitro (for the production of recombinant proteins, for carrying out screening tests, for studying the regulation of genes and the like), ex vivo or in vivo (for the creation of animal models, or in therapeutic approaches). Among these viruses, there may be mentioned in particular adenoviruses, adeno-associated viruses (AAV), retroviruses, herpesviruses or vaccinia viruses.

The Adenoviridae family is widely distributed in mammals and birds and comprises more than one hundred different serotypes of nonenveloped double-stranded DNA viruses possessing a capsid of icosahedral symmetry (Horwitz, In: Fields B N, Knipe D M, Howley P M, ed. Virology. Third edition ed. Philadelphia: Raven Publishers, 1996: 2149–2171). In addition to its safety, the adenovirus has a very broad cellular tropism. Unlike the retrovirus, whose cycle is dependent on cell division, it can infect actively dividing cells such as quiescent cells and its genome is maintained in episomal form. Furthermore, it can be produced at high titres ($10^{11}$ pfu/ml). These major assets of it one makes a most preferred vector for the cloning and expression of heterologous genes. The group C adenoviruses, particularly types 2 and 5, as well as the CAV-2-type canine adenoviruses, whose molecular biology is best known, are the source of the vectors currently used.

The adenovirus has a linear genome of 36 kb, terminating at each of these ends with inverted terminal repeat (ITR) sequences of 103 bp comprising a replication origin as well as an encapsidation signal situated near the left ITR (Shenk, Adenoviridae: The Viruses and Their Replication. In: Fields B N, Knipe D M, Howley P M, ed. Virology. Philadelphia: Raven publishers, 1996: 2111–2148). Three families of genes are expressed during the viral cycle:

The immediate-early genes (E1, E2, E3 and E4) which are involved in the regulation of cellular genes allowing in particular the entry of the cell into the S phase (E1A) and the inhibition of apoptosis (E1B). They are also involved in the regulation of early or late viral genes at the level of the transcription, splicing or transport of the messenger RNAs (E1A, E2A, E4). They also play a role in replication and in escaping the immune response.

The delayed-early genes (pIX and IVa2) are linked to the regulation of transcription of the late genes (IVa2) or to the assembling of the virion (pIX).

The late genes (L1 to L5) are transcribed from the strong promoter (MLP). A primary transcript of 28 kb makes it possible to generate the transcripts corresponding to the various structural proteins (core, penton, hexon) and nonstructural proteins participating in the assembling and in the maturation of the viral particles, by alternative splicing and the use of 5 polyadenylation sites.

Adenoviral vectors have been used for the cloning and expression of genes in vitro (Gluzman et al., Cold Spring Harbor, N.Y. 11724, p. 187), for the creation of transgenic animals (WO95/22616), for the transfer of genes into cells ex vivo (WO95/14785; WO95/06120) or for the transfer of genes into cells in vivo (see in particular WO93/19191, WO94/24297, WO94/08026).

As regards the adeno-associated viruses (AAV), they are relatively small DNA viruses which become integrated into the genome of the cells which they infect, in a stable and relatively site-specific manner. They are capable of infecting a broad spectrum of cells, without inducing any effect on cell growth, morphology or differentiation. Moreover, they do not seem to be involved in pathologies in man. The genome of the AAVs has been cloned, sequenced and characterized. It comprises about 4700 bases and contains, at each end, an inverted terminal repeat (ITR) region of about 145 bases which serves as replication origin for the virus. The remainder of the genome is divided into 2 essential regions carrying the encapsidation functions: the left part of the genome, which contains the rep gene involved in the viral replication and the expression of the viral genes; the right part of the genome, which contains the cap gene encoding the virus capsid proteins.

The use of vectors derived from AAVs for the transfer of genes in vitro and in vivo has been described in the literature (see in particular WO91/18088; WO93/09239; U.S. Pat. Nos. 4,797,368, 5,139,941, EP 488 528).

As regards the retroviruses, they are integrative viruses which selectively infect dividing cells. They therefore constitute vectors of interest for cancer or restenosis applications for example. The genome of retroviruses essentially comprises two LTRs, an encapsidation sequence and three coding regions (gag, pol and env). The construction of recombinant vectors and their use in vitro or in vivo has been widely described in the literature: see in particular Breakfield et al., New Biologist 3 (1991) 203; EP 453242, EP 178220, Bernstein et al. Genet. Eng. 7 (1985) 235; McCormick, BioTechnology 3 (1985) 689, and the like.

For their use as recombinant vectors, various constructs derived from viruses have been prepared, incorporating various genes of interest. In each of these constructs, the viral genome was modified so as to make the virus incapable of autonomously replicating in the infected cell. Thus, the constructs described in the prior art are viruses which are defective for certain regions of their genome which are essential for replication. In particular, as regards adenoviruses, the first-generation constructs exhibit a deletion in/of the E1 region, which is essential for viral replication, at the level of which the heterologous DNA sequences are inserted (Levrero et al., Gene 101 (1991) 195; Gosh-Choudhury et al., Gene 50 (1986) 161). Moreover, to enhance the properties of the vector, it has been proposed to create other deletions or modifications in the adenovirus genome. Thus, a heat-sensitive point mutation was introduced into the ts125 mutant, making it possible to inactivate the 72 kDa DNA binding protein (DBP) encoded by the E2 region (Van der Vliet et al., 1975). Other vectors comprise a deletion of another region essential for the viral replication and/or propagation, the E4 region. Adenoviral vectors in which the E1 and E4 regions are deleted have highly reduced transcription background noise and viral gene expression. Such vectors have been described, for example, in applications WO94/28152, WO95/02697, WO96/22378. Moreover, vectors carrying a modification at the level of the IVa2 gene have also been described (WO96/10088). In addition, so-called "minimum adenovirus" or "pseudo-adenovirus" vectors (or alternatively AdΔ) containing only the regions necessary in cis for the production of the virus (ITR and encapsidation sequences) and lacking any coding viral sequence have also been described (WO94/12649, WO94/28152, WO95/02697), although their production remains very difficult, as explained below.

As regards the AAVs, the vectors described generally lack the entire coding regions Rep and Cap, which are replaced by nucleic acids of interest.

In the recombinant vectors derived from retroviruses, the gag, pol and env genes are generally deleted, completely or in part, and replaced by a heterologous nucleic acid sequence of interest. Moreover, the recombinant retroviruses may comprise modifications at the level of the LTRs in order to suppress the transcriptional activity, as well as large encapsidation sequences, comprising part of the gag gene (Bender et al., J. Virol. 61 (1987) 1639).

Given their defective character in relation to the replication, the production of these various recombinant viruses involves the possibility of transcomplementing the functions deleted from the genome. The transcomplementation is precisely the source of major difficulties for the production of these viruses, and in particular the provision of the transcomplementation functions.

Two approaches have been developed in this regard. The first is based on the construction of transcomplementing lines, that is to say encapsidation lines. The second is based on the use of helper adenoviruses or of helper plasmids.

Various encapsidation lines of defective viruses have been constructed. These lines are capable of producing the functions deficient in the viral vector. Generally, these lines comprise, integrated into their genome, the region(s) deleted from the viral genome (E1, E2 and/or E4 for example for the adenovirus; gag, pol and/or env for the retrovirus, rep and/or cap for the AAV).

One of the lines known for the production of defective adenoviruses is for example the line 293 into which part of the adenovirus genome has been integrated. More precisely, the line 293 is a human embryonic kidney cell line containing the left end (about 11–12%) of the serotype 5 adenovirus (Ad5) genome, comprising the left ITR, the encapsidation region, the E1 region, including E1a and E1b, the region encoding the protein pIX and part of the region encoding the protein pIVa2. This line is capable of transcomplementing recombinant adenoviruses defective for the E1 region, that is to say lacking all or part of the E1 region, and of producing viral stocks having high titres. This line is also capable of producing, at permissive temperature (32° C.), virus stocks comprising, in addition, the heat-sensitive E2 mutation. Other cell lines capable of complementing the E1 region have been described, based in particular on human lung carcinoma cells A549 (WO94/28152) or on human retinoblasts (Hum. Gen. Ther. (1996) 215). Moreover, lines capable of transcomplementing several functions in the adenovirus have also been described. In particular, there may be mentioned lines complementing the E1 and E4 regions (Yeh et al., J. Virol. 70 (1996) 559; Cancer Gen. Ther. 2 (1995) 322; Krougliak et al., Hum. Gen. Ther. 6 (1995) 1575) and lines complementing the E1 and E2 regions (WO94/28152, WO95/02697, WO95/27071).

Various lines have also been described for the production of defective retroviruses, generally capable of expressing the gag, pol and env genes. Such lines are, for example, the PA317 line (U.S. Pat. No. 4,861,719), the PsiCRIP line (WO90/02806), the GP+envAm-12 line (WO89/07150), the BOSC line (WO94/19478) and the like. To construct recombinant retroviruses comprising a nucleic acid of interest, a plasmid comprising in particular the LTRs, the encapsidation sequence and the said nucleic acid is constructed, and then used to transfect an encapsidation line as described above, capable of providing in trans the retroviral functions deficient in the plasmid. The recombinant retroviruses produced are then purified by conventional techniques.

The use of lines can however have certain disadvantages. Thus, it is difficult, expensive and restrictive at the industrial level to construct and to validate such lines. Indeed, these lines should be stable and compatible with industrial uses. Furthermore, the lines described hardly make it possible to avoid the production of replicative contaminant viruses (RCA). Moreover, these lines do not allow at the present time, in a satisfactory manner for an industrial use, very highly defective viral genomes, such as for example minimum adenoviruses as described above, to be transcomplemented. Indeed, the adenovirus has a genome organized into various transcription units whose spatiotemporal regulation is very complex. It has so far not been possible to carry out satisfactorily the transcomplementation of an adenovirus deleted of all the coding viral sequences by expressing each transcription unit separately, in a constitutive or conditional manner, using a cell line. Thus, only a small proportion of the genome corresponding to the E1, E4 and pIX regions, and to the three proteins encoded by E2 (pol, DBP and p-TP) has been constitutively expressed using cell lines. The remainder of the genome corresponds to the major late transcription unit (MLTU) which produces all the messengers for the structural and nonstructural proteins from a primary transcript of 28 kb and is activated after replication of the genome. Now, to generate minimum adenoviruses, transcomplementation of these regions is essential. Neither do these lines make it possible to obtain very high recombinant retrovirus titres.

The second approach consists in cotransfecting with the defective viral genome a construct (plasmid or adenovirus) providing the complementation functions. In particular, the defective recombinant AAVs are generally prepared by cotransfection, in a cell line infected by a human helper virus (for example an adenovirus), of a plasmid containing a nucleic sequence of interest bordered by two AAV inverted terminal repeat (ITR) regions, and of a plasmid carrying the AAV complementation functions (rep and cap genes). Variants have been described in applications WO95/14771; WO95/13365; WO95/13392 or WO95/06743. The disadvantage of using a helper adenovirus lies mainly in the increased risks of recombination between the adenoviral vector and the helper adenovirus, and in the difficulty of separating the recombinant from the helper during the production and purification of the viral stocks. The disadvantage of using a helper plasmid, for example a plasmid Rep/cap, lies in the transfection levels obtained, which do not make it possible to produce high virus titres.

The present application now describes a new system for the production of viruses which makes it possible to overcome these disadvantages. The system of the invention is based on the use of a baculovirus to provide the complementation functions.

The production system according to the invention makes it possible, in a particularly advantageous manner, to dispense with the use of established complementation lines, to avoid the problems of RCA, and to transcomplement highly defective genomes. In addition, the system of the invention is applicable to any cell capable of being infected by the desired virus and by a baculovirus, and thus offers great flexibility of use.

A first subject of the invention therefore consists in a process for the production of defective recombinant viruses according to which the genome of the defective recombinant virus and a baculovirus comprising all or some of the functions necessary for the transcomplementation of the defective recombinant genome are introduced into a population of competent cells.

The process of the invention is therefore based on the use of a baculovirus to provide the complementing functions. Various approaches are possible. It is possible, first of all, to use competent cells not expressing any function of transcomplementation of the defective recombinant genome. In this case, it is possible to use either a baculovirus comprising all the functions necessary for the transcomplementation of the defective recombinant genome, or several baculoviruses each carrying one or more of the functions necessary for the transcomplementation of the defective recombinant genome. It is also possible to use a population of competent cells capable of already transcomplementing one or more functions of the defective recombinant genome (encapsidation line). In this case, the baculovirus(es) used will provide only the functions necessary for the transcomplementation of the defective recombinant genome which are not already transcomplemented by the competent cells.

As indicated above, the advantages of the system of the invention are numerous in terms of industrialization (no need for lines, no RCA, and the like), and in terms of applications (production of recombinant viruses carrying any type of deletion, and particularly of highly defective recombinant adenoviruses). In addition, since the baculovirus does not replicate in human cells, the viral preparation obtained is not contaminated by the baculovirus. Furthermore, the baculovirus being phylogenetically very distant from adenoviruses, there is no risk of recombination or transcomplementation between the two. This system therefore makes it possible, in an advantageous manner, to produce concentrated stocks of defective viruses, lacking RCA. This system is most particularly advantageous for the production of defective recombinant adenoviruses.

Baculoviruses are enveloped, circular double-stranded DNA viruses specific for invertebrates. Their prototype, AcNPV, has a genome of 133 kb. It is widely used as vector for the expression of eukaryotic genes in insect cells, starting from two strong promoters [polyhedrin (Ph) and P10], (King and Possee, The baculovirus expression system. London: Chapman & Hall, 1992.) AcNPV is capable of infecting some mammalian cells, but the genome is neither transcribed nor translated. Recently, Hofmann et al. (PNAS 92 (1995) 10099) have shown that in vitro, hepatocytic cells can be transduced by a purified recombinant baculovirus expressing the LacZ gene. No cellular toxicity was reported, even with a multiplicity of infection of 1000, and the transfection efficiency described in this article is about 50% for an MOI of 100.

The applicant has now shown that it is possible to infect various cell types with a recombinant baculovirus. In particular, the applicant has shown that it was possible, with a recombinant baculovirus, to infect cells of human origin such as immortalized embryonic cells. The applicant has also shown that it is possible to obtain a very high transduction efficiency (>80%). The applicant has also shown that it is possible to introduce, into a baculovirus, functions for complementation of an adenovirus, and to express these functions in a population of competent cells. The applicant has thus made it possible to show that the baculovirus constitutes an inert vector which can be advantageously used for the transfer and expression of virus complementation functions into mammalian, particularly human, cells. Other advantages of the system of the invention are in particular (i) the large cloning capacity which makes it possible to complement a whole adenoviral genome and (ii) the advanced development of the technology of the baculovirus.

The baculovirus carrying the functions for complementation of the virus is also designated in the text which follows helper baculovirus. It may comprise various functions for complementation of the virus.

Thus, the helper baculovirus may comprise the E1 region of the adenovirus. A Baculo-E1 can be used for the production of first-generation adenoviruses, that is to say adenoviruses defective for the E1 region (AdΔE1), regardless of its E3 status (i.e. defective AdΔE1, ΔE3, or not). The production of first-generation defective recombinant adenoviruses (defective for the E1, and possibly E3, region) constitutes a first particularly advantageous application of the process of the invention. As indicated above, various lines have been described in the literature which are capable of transcomplementing the E1 function (cells 293, cells A549, cells 911, and the like). However, various zones of homology exist between the region carrying the transcomplementation functions which is integrated into the genome of the line and the DNA of the recombinant virus which it is desired to produce. Because of this, during production, various recombination events may occur, generating replicative viral particles, in particular type E1+ adenoviruses. This may be a single recombination event followed by breaking of the chromosome, or a double recombination. These two types of modification lead to reintegrating into its initial locus within the adenoviral genome the E1 region contained in the cellular genome. Moreover, given the high titres of recombinant vector which are produced by the line 293 (greater than $10^{12}$), the probability of these recombination events occurring is high. In fact, it has been observed that numerous batches of first-generation defective recombinant adenoviral. vectors were contaminated by replicative viral particles, which may constitute a major disadvantage for pharmaceutical uses. Indeed, the presence of such particles in therapeutic compositions would induce in vivo an uncontrolled viral propagation and dissemination with risks of inflammatory reaction, of recombination and the like. The contaminated batches cannot therefore be used in human therapy.

The present invention makes it possible to overcome these disadvantages. Indeed, according to one embodiment of the process of the invention, the genome of the recombinant adenovirus defective for the E1, and possibly E3, region is introduced into the competent cells, these cells are infected, simultaneously or otherwise, with a baculovirus comprising the E1 region, the adenovirus E1 region present in the baculovirus and the genome of the defective recombinant adenovirus comprising no zone of homology (overlapping) capable of giving rise to recombination. According to this embodiment, it is thus possible to rapidly produce, without an established line, stocks of first-generation recombinant adenoviruses free of RCA. Moreover, as indicated below, the stocks of recombinant adenoviruses thus generated, free of RCA, can be used as starting material for a new production, by coinfection in the competent cells with a baculovirus.

The helper baculovirus may also comprise the E2 region of the adenovirus, in full or in part, particularly the E2a and/or E2b region. A baculo-E2 may be used to produce, in competent cells, adenoviruses defective for the E2 region (Ad-ΔE2), and possibly for the E3 region (Ad-ΔE2, ΔE3). In addition, in competent cells capable of complementing the E1 region of the adenovirus, the baculo-E2 may allow the production of recombinant adenoviruses defective for the E1 and E2 (Ad-ΔE1, ΔE2) and possibly E3 (Ad-ΔE1, ΔE2, ΔE3) regions. Likewise, in competent cells capable of complementing the E1 and E4 regions of the adenovirus (for example in IGRP2 cells), the baculo-E2 may allow the production of recombinant adenoviruses defective for the E1, E2 and E4 (Ad-ΔE1,ΔE2,ΔE4) and possibly E3 (Ad-ΔE1,ΔE2,ΔE3,ΔE4) regions.

The helper baculovirus may also comprise the E4 region (in full or in part) of the adenovirus. A baculo-E4 may be used to produce, in competent cells, adenoviruses defective for the E4 region (Ad-ΔE4), and possibly for the E3 region (Ad-ΔE4,ΔE3). In addition, in competent cells capable of complementing the E1 region of the adenovirus, the baculo-E4 may allow the production of recombinant adenoviruses defective for the E1 and E4 (Ad-ΔE1,ΔE4) and possibly E3 (Ad-ΔE1,ΔE4,ΔE3) regions.

The helper baculovirus may also comprise the E1 and E4 regions (in full or in part) of the adenonvirus. A baculo-E1, E4 may be used to produce, in competent cells, adenoviruses defective for the E1 and E4 (Ad-ΔE1,ΔE4) and possibly E3 (Ad-ΔE1,ΔE4,ΔE3) regions, as illustrated in FIG. 1.

In addition, to generate viruses defective for the E1 and E4 regions, it is also possible to use two helper baculoviruses, one expressing the E1 function, the other the E4 function, in full or in part.

In the same manner, the helper baculovirus may comprise the E1, E2 and E4 regions (in full or in part), and possibly the regions carrying the late genes (L1–L5).

Figure 5:
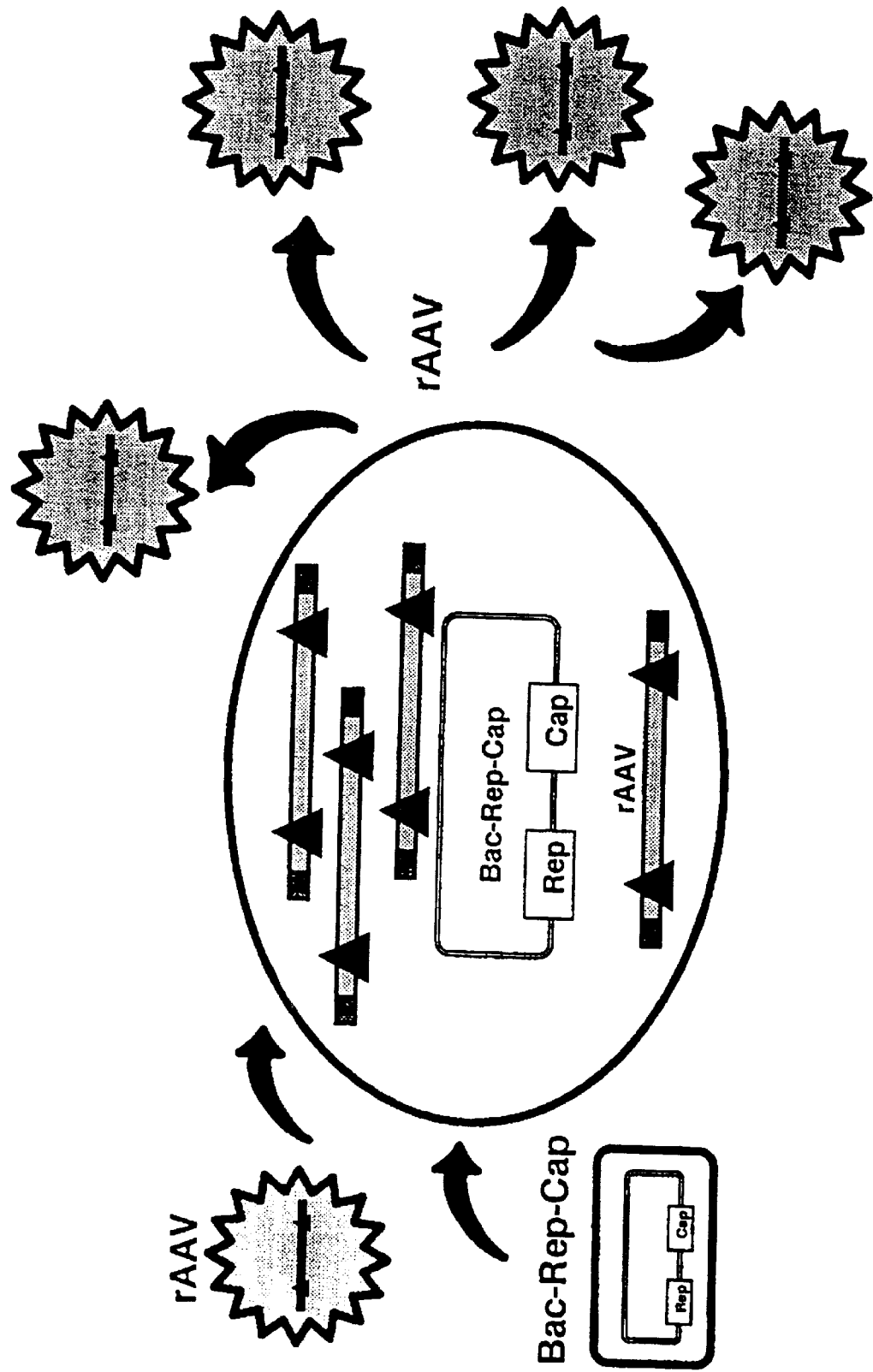

The helper baculovirus may also comprise the AAV R ep and/or Cap regions. A baculo-Rep/Cap thus makes it possible to complement, in a line of competent cells, an AAV genome lacking any coding viral sequence (FIG. 5).

The baculovirus may also comprise the gag, pol and/or env regions of a retrovirus. A baculo-gag/pol/env thus makes it possible to complement, in a line of competent cells, a retroviral genome lacking any coding viral sequence.

It is also possible to use a baculovirus comprising the gag/pol regions and a second baculovirus containing the env region.

In general, it is preferable that the genome of the defective recombinant virus and the complementatibn regions present in the baculovirus do not overlap. This makes it possible, indeed, to avoid the risks of recombination and thus the generation of RCA. This is particularly important for the generation of first-generation adenoviruses (Ad-ΔE1). In this case, the E1 region introduced into the baculovirus is defined so that it does not possess any common sequence with the recombinant genome. To do this, it is possible, for example, to delete from the recombinant genome a region larger than the complementing region inserted into the baculovirus, as illustrated in the examples. This is also advantageous for the generation of Ad-ΔE1,ΔE4 adenovirus.

Thus, in a specific embodiment of the process of the invention, the genome of the defective recombinant virus is introduced into the competent cells, these cells are infected, simultaneously or otherwise, with a baculovirus comprising all or some of the functions necessary for the complementation of the defective genome, the complementation functions present in the baculovirus and the genome of the defective recombinant virus comprising no zone of homology capable of giving rise to recombination. Advantageously, the viral genome is a recombinant adenovirus genome defective for the E1 region and the baculovirus carries a region of the adenovirus capable of transcomplementing the E1 region. According to another variant, the viral genome is a recombinant adenovirus genome defective for the E1 and E4 regions and the baculovirus carries two adenovirus regions capable of transcomplementing the said regions or two baculoviruses are used, one carrying a region of the adenovirus capable of transcomplementing the E1 region and the other a region of the adenovirus capable of transcomplementing the E4 region, without zones of homology with the defective adenoviral genome.

According to a specific embodiment, all the coding regions of the adenovirus are carried by one or more helper baculoviruses. According to a more specific embodiment, only one helper baculovirus comprising all the coding regions of the adenovirus is used. Such a helper baculovirus can thus be used to transcomplement minimum recombinant adenoviruses. Such a baculovirus may in particular comprise the whole of one adenoviral genome, with the exception of the encapsidation region and possibly the ITRs, as illustrated in the examples.

Preparation of the Complementation Functions

The complementation functions introduced into the helper baculovirus may be derived from viruses of different serotypes.

As regards adenoviruses, various serotypes exist whose structure and properties vary somewhat, but which exhibit a comparable genetic organization. More particularly, the complementation functions used for the construction of the baculoviruses according to the invention are derived from an adenovirus of human or animal origin.

As regards adenoviruses of human origin, there may be mentioned, preferably, those classified in the C group. Still more preferably, among the various human adenovirus serotypes, the use of the type 2 or 5 adenoviruses (Ad2 or Ad5) is preferred within the framework of the present invention. It is also possible to use regions derived from type 7 or 12 adenoviruses, belonging to groups A and B. Among the various adenoviruses of animal origin, the use of the adenoviruses of canine origin, and particularly all the strains of the CAV2 adenoviruses [manhattan or A26/61 strain (ATCC VR-800) for example] is preferred within the framework of the invention. Other adenoviruses of animal origin are mentioned in particular in application WO94/26914 incorporated into the present by reference.

In a preferred embodiment of the invention, the complementation function is derived from a group C human adenovirus genome. More preferably, it is derived from the genome of an Ad2 or Ad5 adenovirus.

The regions carrying the various complementation functions may be obtained, from an adenoviral genome, by enzymatic cleavages according to methods known to persons skilled in the art. These regions may optionally be modified in order to reduce their size, or to replace certain regulatory elements (promoter, enhancer and the like) with heterologous elements. In general, these regions are prepared as follows: the DNA of an adenovirus is purified by caesium chloride gradient centrifugation or obtained in vitro from a prokaryotic (WO96/25506) or eukaryotic (WO95/03400) plasmid. The DNA is then cleaved with appropriate restriction enzymes and the fragments obtained, carrying the desired complementation functions, are identified and selected. The choice of the restriction enzymes used depends on the desired complementation functions. It is then guided by the restriction maps and the published sequences of the adenoviral genomes. Thus, the E1 region may be isolated in the form of fragments carrying all the reading frames of E1A and E1B downstream of the E1A promoter. The E4 region may be isolated in the form of fragments carrying the whole of the reading frames, or only part of them, and preferably the frames ORF3 or ORF6 or ORF6-ORF6/7.

Similar methodologies are used to prepare the AAV and recombinant retrovirus complementation regions. Thus, the AAV rep and/or cap regions may be obtained by enzymatic cleavage from the viral DNA isolated from various AAV serotypes. This is preferably AAV-2. For retroviruses, the gag, pol and/or env regions may also be obtained according to conventional molecular biological techniques, from various types of retroviruses, such as in particular MoMuLV (Murine Moloney Leukaemia Virus; also called MOMLV), MSV (Murine Moloney Sarcoma Virus), HaSV (Harvey Sarcoma Virus); SNV (Spleen Necrosis Virus), RSV (Rous Sarcoma Virus) or Friend's virus.

Construction of the Helper Baculovirus

The fragments carrying the complementation regions are then subcloned into a plasmid vector allowing their manipulation (finer digestions, PCR, additions of regulatory sequences, and the like), for example in a prokaryotic or eukaryotic organism. The final fragment obtained, encoding the complementation function(s) is then introduced into the helper baculovirus using conventional molecular biological techniques. Specifically, the fragment is cloned between two sequences homologous to a region of the genome of a baculovirus, and then the resulting fragment or plasmid is cotransfected with the genome of a baculovirus into insect cells (conventionally Sf9 and Sf21, spodoptera frugiperda cells, but also Tn-368 and High-Five™ BTI-TN-5B1-4 (Gibco), trichopulsia ni cells, or any other insect cell permissive to baculoviruses and capable of being used for their production). The homologous recombination between the plasmid or fragment and the genome of the baculovirus generates the desired recombinant baculovirus, which may be recovered and purified according to conventional methods (see in particular King and Possee: the baculovirus expression system. London: Chapman & Hall, 1992). For the construction of the recombinant baculoviruses, various kits comprising shuttle vectors are commercialized and may be used according to the recommendations of the manufacturers. In particular, it is possible to use the shuttle vectors pBAC marketed by the company Clontech, the vectors pAc (Verne et al., Bio/Technology 6 (1988) 47, Pharmingen, USA), the vectors pBlue-Bac (Invitrogen) or the vectors pBSV (Boehringer). The complementation functions may thus be inserted into different sites of the baculovirus, and in particular into the locus of the polyhedrin gene or of the p10 gene. Moreover, various baculovirus strains can be used, such as in particular AcNPV or Bombyx mori (Maeda et al., Nature 315 (1988) 592). Furthermore, the baculovirus used may be modified to enhance/change its tropism. It is indeed possible to modulate the tropism of the viral vectors by modifying their surface proteins so as (i) to limit it by fusion of the viral proteins with a specific ligand (light immunoglobulin chain, Gastrin-Releasing Peptide) or (ii) to broaden it by formation of pseudotypes with a heterologous viral glycoprotein [G of the Vesicular Stomatitis Virus (VSV)], [Liu et al., J. Virol 70(4) (1996) 2497; Michael et al., Gene Ther. 2 (1995) 660]. Recently, it was shown that the baculovirus surface glycoprotein (gp64) fused with gp120 of the HIV virus was capable of binding to the CD4 receptor (Boublik et al. Bio/Technology 13 (1995) 1079). This modification of gp64 does not affect the viability of the baculovirus in insect cells. A similar construct with the G of VSV should make it possible to enhance the tropism of the baculovirus for mammalian cells and therefore to increase the transduction efficiency of the Huh7 cells as well as other cell lines.

In the helper baculovirus, the complementation functions are advantageously placed under the control of a heterologous promoter (i.e. of a different origin from the baculovirus), which is functional in competent cells. It appears, indeed, that the baculovirus promoters do not make it possible to obtain sufficient levels of expression of the complementation functions in cells other than insect cells, and are therefore not the most appropriate for the applications of the invention. The promoter may first of all be the actual promoter (homologous promoter) of the complementation functions of the virus (E1A, E4, E2, MLP promoter for the adenovirus, P5 or P19 promoters of AAV, the LTR promoter of RSV, and the like). It may also be any promoter of different origin which is functional in the competent cell used. To this effect, there may be mentioned for example the promoters of genes expressed in this cell, or known ubiquitous promoters such as for example the promoter of the PGK gene, the immediate-early promoter of CMV, the promoter of the TK gene of the herpesvirus or alternatively the LTR promoter of RSV. It may also be a regulated promoter, such as for example the promoter of the MMTV virus, a promoter responding to hormones, for example of the GRE5 type, or a promoter regulated by tetracycline (WO). Advantageously, it is an inducible or strong ubiquitous, homologous promoter.

Thus, another subject of the present invention relates to a recombinant baculovirus comprising, inserted into its genome, a nucleic acid encoding a complementation function of a virus placed under the control of a heterologous promoter. More particularly, the complementation function is a protein necessary for the production of the said virus, and whose coding region is inactive (mutated, deleted and the like) in the defective viral genome. For adenoviruses, the complementation function is more particularly chosen from all or some of the functions encoded by the E1, E2, E4, L1–L5, pIX and IVa2 regions of the adenovirus, alone or in combination. For the AAV, they are functions encoded by the Rep and/or Cap regions; and for the retrovirus, gag, pol and/or env. Advantageously, the nucleic acid corresponds to a region of a viral genome comprising the region encoding the complementation function chosen. In particular, it is a fragment of a genome of adenoviruses of serotype Ad2 or Ad5, MoMLV or AAV-2. In a particularly preferred manner, the nucleic acid also comprises the promoter region which is naturally responsible for the expression of the complementation functions chosen.

By way of a specific example, the present invention relates to a baculovirus comprising all or part of the E1 region of an adenovirus. More particularly, it is a baculovirus comprising the E1a, E1b or E1a and E1b region. The E1 region of the adenovirus is located at the level of nucleotides 104 (promoter E1a) to 4070 (polyA E1b) of Ad5. In particular, the TATA box of the E1a promoter is located at the level of nucleotide 470, the ATG codon of E1a at the level of nucleotide 560, and the stop codon E1b at the level of nucleotide 3511. There may be mentioned by way of precise example a baculovirus comprising a fragment 391-3511. This helper baculovirus is particularly suitable for the production of recombinant adenoviruses defective for the E1 region, carrying a larger deletion than this 391-3511 fragment. In particular, it is suitable for the production of first-generation adenoviruses, without RCA, carrying a deletion in the E1 region covering nucleotides 383-3512 inclusive.

Another specific example of a baculovirus according to the invention comprises, for example, all or some of the E1 and E4 regions of the adenovirus. The E4 region of the adenovirus consists of 7 open reading frames, designated ORF1, ORF2, ORF3, ORF4, ORF3/4, ORF6 and ORF6/7. Among the proteins encoded by these various ORFs, those produced by ORF3 and ORF6 appear to allow the "replication" of the virus, and therefore the transcomplementation of an adenovirus defective for the E4 region, even in its entirety. As a result, the helper baculovirus of the invention advantageously comprises all the E4 region or only part thereof comprising at least the ORF3 or ORF6 frame. The various parts of the E4 region may be obtained by enzymatic cleavages or modified according to methods known to persons skilled in the art. In particular, the reading frame ORF6 may be isolated from the E4 region in the form of a BglII-PvuII fragment, corresponding to nucleotides 34115-33126, and the reading frames ORF6-ORF6/7 may be isolated from the E4 region in the form of a BglII-BglII fragment corresponding to nucleotides 34115-32490 of the genome of Ad5. The baculovirus may also comprise the whole of the reading frames ORF1–ORF7 (for example in the form of a 32800-35826 or 32811-35614 or 32811-35640 fragment). It is understood that other fragments may be determined on the basis of published sequences of the adenoviral genomes. The use of a baculovirus carrying a reduced unit of the E4 region is advantageous because it allows the transcomplementation of a defective adenoviral genome carrying a larger deletion of the E4 region, therefore without a zone of homology, and thus to avoid any possibility of recombination.

According to a first embodiment, the nucleic acid encoding the complementation function(s) is introduced into the helper baculovirus in the form of an expression cassette. This embodiment is the easiest to use. It is particularly suitable for the production of recombinant adenoviruses defective for immediate-early genes and for the production of defective recombinant AAVs and retroviruses.

According to another embodiment, the nucleic acid encoding the complementation function(s) is introduced into the helper baculovirus in the form of an excisable cassette, generating a replicative molecule in the competent cell. The replication of the cassette in the cell makes it possible advantageously to increase the copy number of the complementing genes, and thus to enhance the production levels of the system. This embodiment is particularly suitable for the production of very highly defective recombinant adenoviruses, particularly defective for the structural genes. In particular, this embodiment is particularly suitable for the production of "minimum" adenoviruses. Indeed, the quantity of structural protein is a limiting factor for the production of high titres of highly defective adenoviruses (minimum adenovirus type). This embodiment makes it possible, for the first time, to considerably increase the intracellular levels of transcomplementing proteins, particularly of structural proteins of the adenovirus (encoded by the L1 to L5 regions), up to levels compatible with the transcomplementation of minimum adenoviruses.

Thus, the applicant has shown that it is possible to construct recombinant baculoviruses comprising a heterologous region capable of being excised in a cell, preferably in an inducible and regulated manner, in order to generate a circular and replicative molecule (of episomal type).

The excision is advantageously carried out by a site-specific recombination mechanism, and the replication in the cell is brought about by a replication origin, independent of the state of cell division.

More preferably, the site-specific recombination used according to the process of the invention is obtained by means of two specific sequences which are capable of recombining with each other in the presence of a specific protein, generally called recombinase. These specific sequences, arranged in the appropriate orientation, flank in the baculovirus the sequences encoding the complementation functions. Thus, the subject of the invention is also a recombinant baculovirus comprising, inserted into its genome, at least one DNA region flanked by two sequences allowing a site-specific recombination and positioned in direct orientation, the said DNA region comprising at least one replication origin functional in competent cells and a nucleic acid encoding a complementation function of a virus.

The sequences allowing the recombination which are used in the framework of the invention generally comprise from 5 to 100 base pairs, and more preferably less than 50 base pairs. They may belong to different structural classes, and in particular to the family of the recombinase of the P1 bacteriophage or of the resolvase of a transposon.

Among the recombinases belonging to the bacteriophage 1 integrase family, there may be mentioned in particular the integrase of phages lambda (Landy et al., Science 197 (1977) 1147), P22 and F80 (Leong et al., J. Biol. Chem. 260 (1985) 4468), HP1 of *Haemophilus influenzae* (Hauser et al., J. Biol. Chem. 267 (1992) 6859), the Cre integrase of the P1 phage, the integrase of the plasmid pSAM2 (EP 350 341) or the FLP recombinase of the plasmid 2 μm of the yeast *Saccharomyces cerevisiae*.

Among the recombinases belonging to the Tn3 transposon family, there may be mentioned in particular the resolvase of the Tn3 transposon or of the gd, Tn21 and Tn522 transposons (Stark et al., 1992); the Gin invertase of the mu bacteriophage or the resolvase of plasmids, such as that of the fragment par of RP4 (Abert et al., Mol. Microbiol. 12 (1994) 131).

According to a preferred embodiment, in the recombinant baculoviruses of the present invention, the sequences allowing the site-specific recombination are derived from a bacteriophage. More preferably, they are sequences for attachment (attp and attB sequences) of a bacteriophage or of derived sequences. These sequences are capable of specifically recombining with each other in the presence of a recombinase called integrase. By way of specific examples, there may be mentioned in particular the sequences for attachment of the phages lambda, P22, F80, P1, HP1 of *Haemophilus influenzae* or of the plasmid pSAM2, or 2 μm.

Still more preferably, the sequences allowing the site-specific recombination are represented by the recombination system of the P1 phage. The P1 phage possesses a recombinase called Cre which specifically recognizes a nucleotide sequence of 34 base pairs called lox P site (Sternberg et al., J. Mol. Biol. 150 (1981) 467). This sequence is composed of two palindromic sequences of 13 bp separated by a conserved sequence of 8 bp. The site-specific recombination is advantageously obtained using LoxP sequences or derived sequences, and the Cre recombinanse.

The term derived sequence includes the sequences obtained by modification(s) of the recombination sequences above, conserving the capacity to specifically recombine in the presence of the appropriate recombinase. Thus, it may involve reduced fragments of these sequences or on the contrary fragments extended by addition of other sequences (restriction sites and the like). It may also involve variants obtained by mutation(s), particularly by point mutation(s).

According to a preferred embodiment of the invention, the sequences allowing a site-specific recombination are therefore LoxP sequences of the P1 bacteriophage, and the recombination is obtained in the presence of the Cre protein. In this regard, the recombination may be obtained by bringing the competent cells directly into contact with the Cre recombinase, or by expression of the gene encoding the Cre recombinase in the competent cells. Advantageously, the Cre recombinase is produced in the cell by inducing the expression of the corresponding gene. Thus, the gene encoding the recombinase is advantageously placed under the control of an inducible promoter, or constructed in a regulatable form. In this regard, there is advantageously used a fusion between Cre and the steroid hormone (oestradiol, progesterone and the like) binding domain allowing the activity of Cre to be regulated and therefore the recombination event to be induced (Metzger et al., PNAS 92 (1995) 6991). More generally, the expression of the recombinase may be controlled by any strong promoter, regulated or otherwise. The expression cassette may be transfected into the competent cells, or integrated into the genome of the competent cells, as illustrated in the examples.

This system therefore makes it possible to generate replicative molecules producing, in the competent cells, high levels of virus, particularly adenovirus, complementation function. This type of construct is particularly suitable for the complementation of highly defective genomes, in particular of adenoviral genomes defective for the late genes. Thus, a specific construct according to the invention is represented by a baculovirus comprising, inserted into its genome, at least a DNA region flanked by two LoxP sequences positioned in direct orientation, the said DNA region comprising at least one replication origin functional in the competent cells and one nucleic acid encoding a complementation function of an adenovirus. Advantageously, the complementation functions comprise all or some of the immediate-early genes present in the E1, E2 and E4 regions. Still more preferably, the complementation functions comprise all or some of the immediate-early genes and of the delayed-early genes. Preferably, the complementation functions allow the complementation of a recombinant adenovirus lacking any coding viral sequence. In particular, the complementation functions consist of the whole of the adenoviral genome, with the exception of the ITRs and of the packaging region. According to a specific variant, the complementation functions consist of a complete adenoviral genome lacking, however, the packaging region (Ad.Psi-). This genome comprises in particular the ITRs which serve for the replication of the genome in the competent cells, after excision.

To bring about the replication of the episomal molecule, the latter therefore contains a replication origin functional in the competent cells used. This replication origin preferably consists of the actual ITR sequences of the adenovirus, which allow substantial amplification of the molecule. It may also be another replication origin allowing, preferably, amplification by a factor greater than 20 of the viral DNA in the competent cell. There may be mentioned, by way of illustration, the origin OriP/EBNA1 of the EBV virus or the E2 region of the papilloma virus. It is understood that the ITR sequences of the adenovirus constitute a preferred embodiment.

For carrying out the process of the invention, the helper baculovirus(es) are generally used at a Multiplicity of Infection (MOI) allowing a large population of cells to be infected, without significantly impairing cell viability. Generally, it is more particularly between 10 and 1000. The MOI corresponds to the number of viral particles per cell. The MOI may be easily adjusted by persons skilled in the art depending on the competent cells used, essentially on the basis of two criteria: the infection efficiency and the possible toxicity. Advantageously, the MOI used for the helper baculovirus is between 20 and 500.

Introduction of the Viral Genome

As indicated above, the process of the invention comprises the introduction, into competent cells, of the helper baculovirus and of the recombinant viral genome. In this regard, the genome of the defective recombinant adenovirus may be introduced in various ways into the competent cell.

It may, first of all, be a purified defective recombinant adenovirus, advantageously free of RCA. In this case, the competent cells are infected with the defective recombinant adenovirus and with the helper baculovirus. The infection with the recombinant adenovirus makes it possible to introduce into the competent cell the corresponding genome, which is then amplified and encapsidated in order to produce stocks at a high titre, free of RCA. This embodiment is particularly advantageous for generating first-generation viruses (Ad-ΔE1; Ad-ΔE1, ΔE3). Indeed, these viruses are difficult to produce at high titres, without contamination with RCAs. According to the process of the invention, it is now possible, starting with a first-generation defective recombinant adenovirus, by coinfection in a competent cell with a baculovirus comprising the E1 region, to obtain concentrated stocks, of high quality. This embodiment is also advantageous for the production of viruses defective in two or three essential regions of their genome (E1, E2, E4 in particular). In general, this embodiment is advantageous because the efficiency of infection with the adenovirus is very high (greater than the efficiency of transfection with DNA), and therefore makes it possible to generate concentrated stocks. In this embodiment, the recombinant adenovirus and the recombinant baculoviruses are used at multiplicities of infection (MOI) allowing a large population of cells to be infected, without significantly impairing cell viability. The MOI used for the baculovirus is that stated above (between 10 and 1000). As regards the adenoviruses, it is advantageously between 1 and 1000, preferably between 1 and 500, still more preferably between 1 and 100. The MOI used for the adenovirus is also adjusted according to the cell type chosen. The MOI range may be easily determined by persons skilled in the art using, for example, an adenovirus and a baculovirus comprising a separate marker gene, in order to measure the efficiency of infection and any competition. More preferably, the MOI of the adenovirus is less than 50, for example between 1 and 20.

According to another particularly advantageous embodiment, the genome of the defective recombinant adenovirus is introduced in the form of DNA. In this case, the genome is introduced by transfection, optionally in the presence of a transfection-facilitating agent (lipids, calcium phosphate and the like). The recombinant genome thus introduced may be prepared in vitro according to various techniques, and in particular in *E. coli* (WO96/25506) or in a yeast (WO95/03400). This embodiment is in particular useful for generating a first batch of defective recombinant virus, free of RCA, which can then in turn be used to produce stocks with a high titre according to the preceding embodiment.

The genome of the defective recombinant adenovirus may also be introduced using another recombinant baculovirus. According to this embodiment, the genome of the defective recombinant adenovirus is prepared in vitro, for example as indicated above, and then introduced into a baculovirus, in the form of a cassette capable of being excised in the competent cell. According to this embodiment, the competent cells are put in the presence of a baculovirus carrying the genome of the defective recombinant adenovirus, and of one or more helper baculoviruses (carrying the complementation functions). This embodiment is particularly advantageous for the production of highly defective recombinant adenoviruses. By virtue of this system, it is indeed possible to introduce into the population of competent cells high quantities both of the highly defective recombinant genome and of the corresponding complementation functions.

In this regard, a process of the invention therefore comprises the coinfection of competent cells with a baculovirus carrying the genome of the defective recombinant adenovirus, and one or more helper baculoviruses carrying the complementation functions. The MOI values used in this embodiment are also between 10 and 1000 for each of the baculoviruses used.

Two types of constructs have been prepared in the prior art for the production of minimum adenoviruses: (1) the transgene (β-galactosidase) cloned between the ITRs, bordered by a unique restriction site or (2) the right and left ITRs cloned in direct orientation in 5' of the transgene (Fisher et al., Virology 217 (1996) 11; Kumar-Singh et al., Hum. Mol. Genet. 5 (1996) 913). Minimum adenoviruses were produced in the cells 293 by transfection of linearized (1) or circular (2) DNA, the viral proteins necessary for the replication and for the encapsidation of the minigenome being provided in trans by a helper virus (AdΔE1). The minimum adenoviruses behave like interfering defective (ID) particles and are progressively amplified during successive passages. The major problem posed by the use of this methodology is the separation of the two types of particles produced, responsible for the contamination of the stocks by the helper virus, and the very low titres of minimum adenoviruses thus obtained (less than $10^8$ pfu/ml).

The present application makes it possible, for the first time, to generate minimum adenoviruses using a baculovirus to deliver the adenoviral minigenome and a baculovirus to provide all the transcomplementation functions (complementing genome).

The recombinant adenoviral genome is advantageously introduced into the baculovirus, between two sequences allowing a site-specific recombination in the competent cells, as described for the helper baculovirus.

Figure 2:
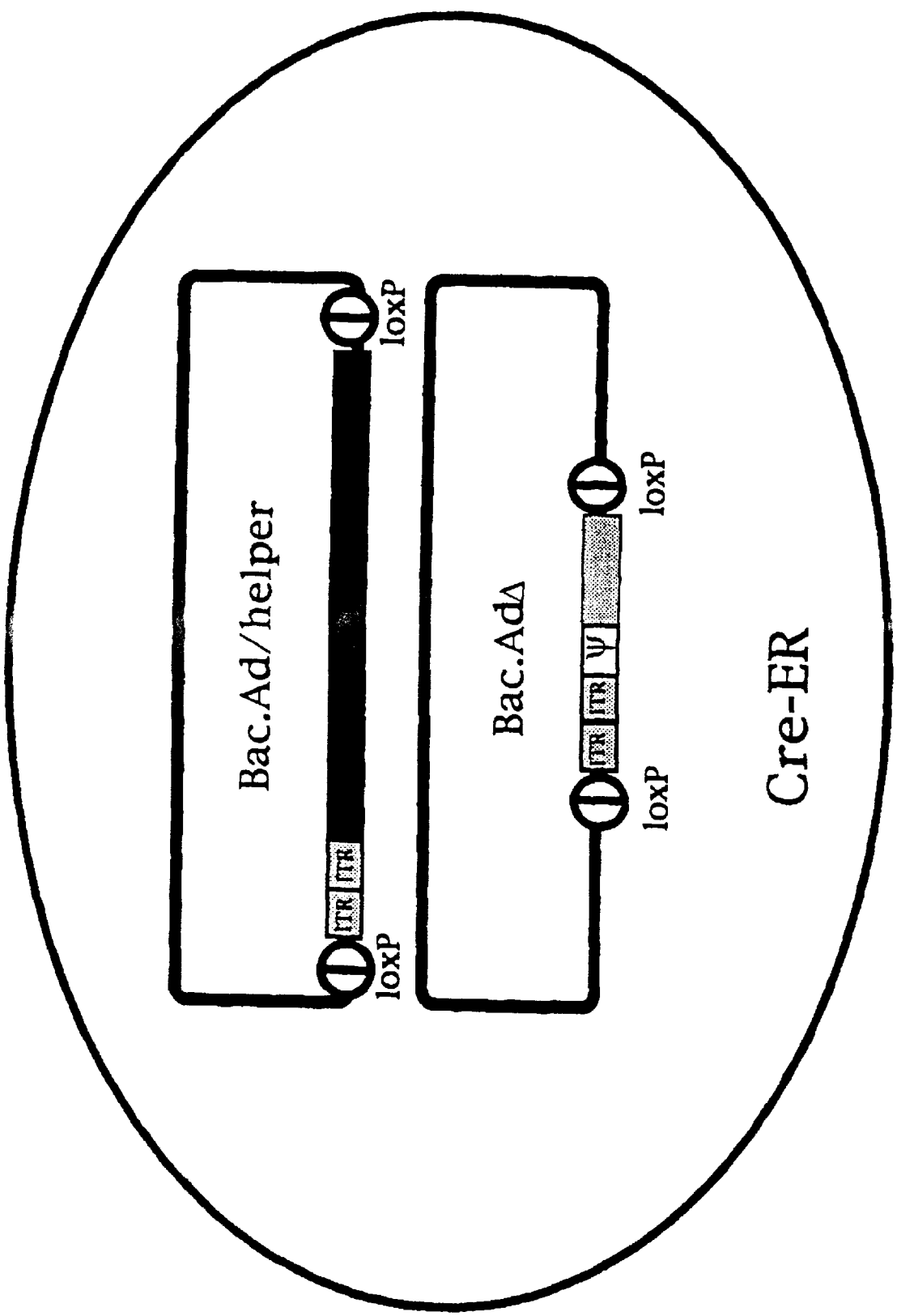
Figure 3:
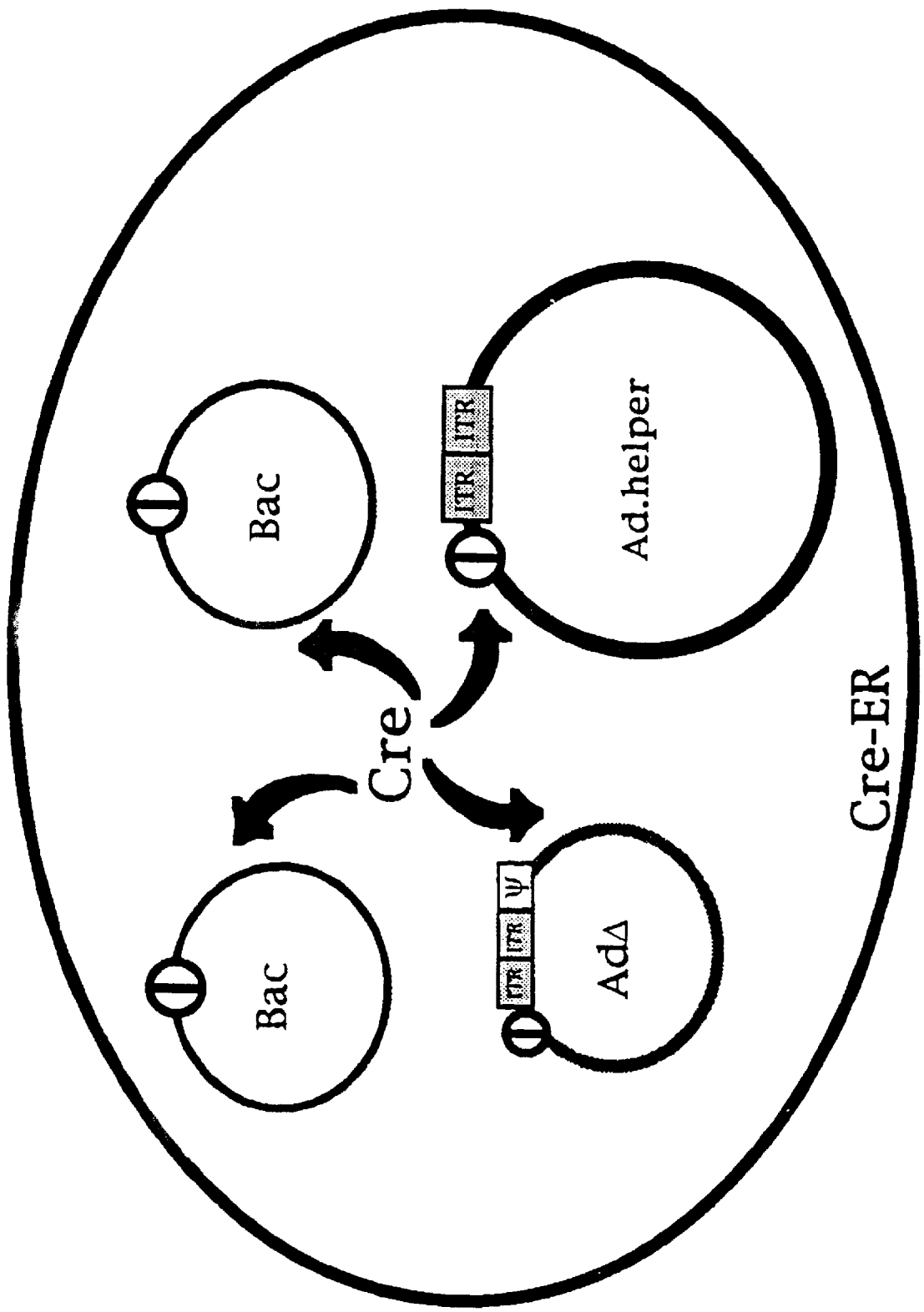
Figure 4:
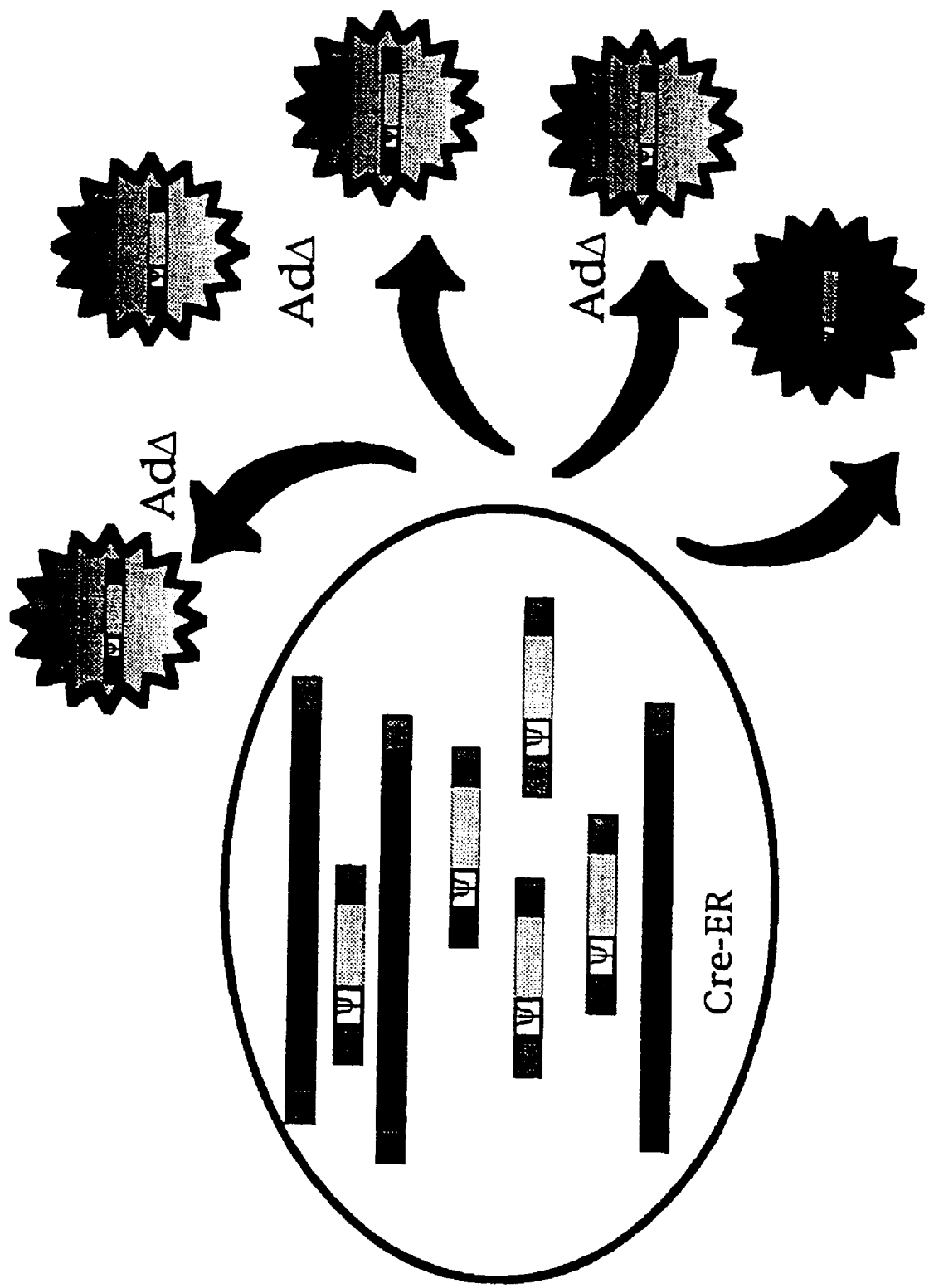

The present application describes in particular a system for the production of a minimum adenovirus using a baculovirus to deliver the adenoviral minigenome with the aid of the loxP/Cre system and a baculovirus to provide all the transcomplementation functions (complementing genome), also with the aid of a Cre/loxP system (see FIGS. 2–4).

According to another embodiment, the site-specific recombination system used to deliver the complementation functions is different from that used to deliver the genome of the recombinant adenovirus. In particular, the LoxP/Cre system may be used to deliver the defective adenoviral genome and the AttP/AttB system to deliver the complementation function(s).

The process of the invention thus makes it possible to construct an adenoviral vector deleted of all coding viral sequences and comprising only the ITRs and the encapsidation signal (minimum adenoviruses). This vector can theoretically accommodate up to 37 kb of exogenous sequence whereas the cloning capacity of current vectors does not exceed 8.5 kb. It thus makes it possible to clone genes of large size such as the dystrophin gene (14 kb) with all their regulatory elements (promoter, enhancer, introns and the like) so as to obtain an optimum expression, in the target tissue. Furthermore, the absence of any immunogenic viral sequence should increase the duration of expression of the transgene in quiescent tissues.

The genome of AAV or the defective retrovirus may also be introduced in the form of a virus, a genome or a plasmid, according to the techniques described above.

Competent Cells

The process of the invention may be carried out in various types of cells. For the purposes of the invention, "competent cell" is understood to mean a cell permissive to infection by the baculovirus and the virus to be produced, and allowing a productive viral cycle for the latter. The capacity to infect cells with these viruses can be determined using recombinant viruses expressing a marker gene such as the E. coli LacZ gene. It is preferably a mammalian cell, still more preferably a cell of human origin. The competent cells used may be quiescent cells or actively dividing cells, established lines or primary cultures. They are advantageously mammalian cells compatible with an industrial use, that is to say without a known pathogenic character, capable of being cultured and, where appropriate, of being stored under appropriate conditions. Advantageously, the cells used are hepatic, muscular, fibroblastic, embryonic, nerve, epithelial (pulmonary) or ocular (retinal) cells. There may be mentioned, by way of nonlimiting example, the cells 293 or any derived cell comprising an additional complementation function (293E4, 293E2a, and the like), the A549 cells, the HuH7 cells, the Hep3B cells, the HepG2 cells, the human retinoblastic cells (HER, 911), the HeLa cells, the 3T3 cells or the KB cells.

To carry out the process of the invention, the genome of the recombinant virus and the baculovirus may be introduced into the population of competent cells simultaneously or spaced out over time. Advantageously, the cells are brought into contact both with the recombinant genome and the helper baculovirus. In the case of a system generating replicative molecules in vivo, the recombinase is introduced or expressed beforehand, simultaneously or subsequently.

The production of the viruses generally leads to the lysis of the cells. The viruses produced can therefore be harvested after cell lysis, according to known purification methods. They can then be packaged in various ways depending on the desired use. Moreover, to avoid any risk of contamination of the viral stock with possible traces of baculoviruses that have not penetrated into the competent cells (helper baculovirus or baculovirus providing the recombinant viral genome), it is possible to apply the following techniques:

it is possible to purify the adenoviruses by chromatography according to the method described in application FR96/08164. This technique makes it possible to separate the adenovirus from any possible residual baculovirus;

it is also possible to cause organic solvents (for example ether, chloroform) to act on the stocks of purified adenovirus. Indeed, the baculovirus is an enveloped virus (glycoprotein envelope), and is therefore very sensitive to any organic solvent (which extracts the lipids from its envelope); in contrast, the adenovirus is not enveloped, and the same solvents have no effect on it;

it is also possible, by CsCl gradient purification, to separate, by density, any residual baculovirus and the recombinant virus.

These three methods can be used independently or conjointly. Moreover, any other method known to a person skilled in the art can also be used.

Use of the Viruses

The viruses thus produced can be used for the cloning, transfer and expression of genes in vitro, ex vivo or in vivo. Such genes of interest are, for example, genes encoding enzymes, blood derivatives, hormones, lymphokines: interleukins, interferons, TNF, and the like (FR 9203120), growth factors, neurotransmitters or their precursors of synthesis enzymes, trophic factors: BDNF, CNTF, NGF, IGF, GMF, aFGF, bFGF, NT3, NT5, and the like, apolipo proteins: ApoAI, ApoAIV, ApoE, and the like (WO94/

25073), dystrophin or a minidystrophin (WO93/06223), tumour suppressor genes: p53, Rb, Rap1A, DCC, k-rev, and the like (WO94/24297), genes encoding factors involved in clotting: Factors VII, VIII, IX and the like, suicide genes: thymidine kinase, cytosin deaminase and the like, or all or part of a natural or artificial immunoglobulin (Fab, ScFv, and the like, WO94/29446), and the like. The gene of interest may also be a gene or an antisense sequence, whose expression in the target cell makes it possible to control the expression of genes or the transcription of cellular mRNAs. Such sequences may, for example, be transcribed, in the target cell, into RNAs complementary to cellular mRNAs and thus block their translation into protein, according to the technique described in Patent EP 140 308. The gene of interest may also be a gene encoding an antigenic peptide, capable of generating an immune response, for the production of vaccines. It may be in particular antigenic peptides specific for the Epstein-Barr virus, the HIV virus, the hepatitis B virus (EP 185 573), the pseudorabies virus, or specific for tumours (EP 259 212). The gene may be any DNA (gDNA, CDNA and the like) encoding a product of interest, potentially including the appropriate expression signals (promoter, terminator and the like).

These viruses may be used in vitro for the production of these recombinant proteins. They may also be used, still in vitro, to study the mechanism of action of these proteins or to study the regulation of the expression of genes or the activity of promoters. They may also be used in vivo, for the creation of animal models or of transgenic animals. They may also be used for the transfer and expression of genes in vivo, in animals or man, in gene or cell therapy procedures.

The present application will be described in greater detail with the aid of the following examples which should be considered as illustrative and nonlimiting.

LEGEND TO THE FIGURES

FIG. 1: Schematic representation of the production of a third-generation defective recombinant adenovirus (defective for the E1 and E4 functions) using a baculo-E1, E4.

FIGS. 2–4: Schematic representation of the production of a minimum adenovirus using a first baculovirus to introduce the defective adenoviral genome and a second baculovirus to introduce the compleentation functions.

FIG. 5: Schematic representation of the production of a recombinant AAV defective for the Rep and Cap functions using a baculo-Rep/Cap.

EXAMPLES

1. Cells Used

The cells used within the framework of the invention may be obtained from any cell line or population capable of being infected by an adenovirus or an AAV or a retrovirus or by a baculovirus, compatible with a use for therapeutic purposes. It is more preferably a mammalian, particularly human, cell. There may be mentioned more particularly:

The cells of the 293 line:

The 293 line is a human embryonic kidney cell line containing the left end (about 11–12%) of the genome of the serotype 5 adenovirus (Ad5), comprising the left ITR, the encapsidation region, the E1 region, including E1a, E1b, the region encoding the pIX protein and part of the region encoding the pIVa2 protein (Graham et al., J. Gen. Virol. 36 (1977) 59). This line is capable of transcomplementing recombinant adenoviruses defective for the E1 region, that is to say lacking all or part of the E1 region, and of producing viral stocks having high titres.

The cells of the A549 line

Cells complementing the E1 region of the adenovirus were constructed from A549 cells (Imler et al., Gene Ther. (1966) 75). These cells contain a restricted fragment of the E1 region, lacking the left ITR, placed under the control of an inducible promoter.

The cells of the HER line

The human embryonic retinal (HER) cells can be infected with an adenovirus (Byrd et al., Oncogene 2 (1988) 477). Adenovirus encapsidation cells prepared from these cells have been described for example in application WO94/28152 or in the article by Fallaux et al. (Hum. Gene Ther. (1996) 215). There may be mentioned more particularly the 911 line comprising the E1 region of the genome of the Ad5 adenovirus, from nucleotide 79 to nucleotide 5789, integrated into the genome of HER cells. This cell line allows the production of viruses defective for the E1 region.

The IGRP2 cells

The IGRP2 cells are cells obtained from cells 293, by integration of a functional unit of the E4 region under the control of an inducible promoter. These cells allow the production of viruses defective for the E1 and E4 regions (Yeh et al., J. Virol (1966) 70).

The VK cells

The VK cells (VK2-20 and VK10-9) are cells obtained from cells 293, by integration of the entire E4 region under the control of an inducible promoter, and the region encoding the protein pIX. These cells allow the production of viruses defective for the E1 and E4 regions (Krougliak et al., Hum. Gene Ther. 6 (1995) 1575).

The 293E4 cells

The 293E4 cells are cells obtained from cells 293, by integration of the entire E4 region. These cells allow the production of viruses defective for the E1 and E4 regions (WO95/02697; Cancer Gene Ther. (1995) 322).

The Sf9 and Sf21 cells are embryonic Lepidoptera cells. These cells are accessible in collections (No. CRL-1711 ATCC) as well as their culture conditions. They are also commercially available (Gibco). See also King and Possee: The baculovirus expression system, London: Chapman and Hall, 1992.

The human hepatocytic cells

The HepG2 and Hep3B and HuH7 cells are human lines derived from hepatocarcinomas. They are accessible in depository collections and their properties have been described for example in U.S. Pat. Nos. 4,393,133 and 4,393,133.

Human cell line KB:

Derived from a human epidermal carcinoma, this line is accessible at the ATCC (ref. CCL17) as well as the conditions allowing its culture.

Human cell line Hela:

Derived from a carcinoma of the human epithelium, this line is accessible at the ATCC (ref. CCL2) as well as the conditions allowing its culture.

Cell line W162:

These cells are Vero cells comprising, integrated into their genome, the E4 region of the Ad2 adenovirus. These cells have been described by Weinberg et al., (PNAS 80 (1983) 5383).

2. Infection of Human Cells with a Recombinant Baculovirus

This example describes the capacity of baculoviruses to infect cells of human origin.

Human cells (particularly 293 or derivatives thereof) are infected with various dilutions of a solution of recombinant baculovirus expressing the LacZ gene under the control of the RSV LTR. 48 hours after infection, the appearance of blue cells is revealed, demonstrating the infectability of these cells by a baculovirus.

3. Construction of Baculoviruses Expressing the E1 Region of the Adenovirus and of a Corresponding Defective Adenovirus 3-1 Cloning of two cassettes for the expression of E1

The plasmid AE2 is obtained from the cloning, in PCRII (Invitrogen) of the product of the PCR performed on pBRE1 with the oligonucleotides 5'-TCCTTGCATTTGGGTAACAG-3' and 5'-GCGGCCGCTCAATCTGTATCTTC-3'; this PCR product contains nucleotides 3198 to 3511 of Ad5, that is to say the 3' end of the E1B region. The plasmid pBRE1 contains nucleotides 1 to 5788 of Ad5 cloned into pBR322, deleted roughly of nucleotides 1300 to 2300.

The plasmid AE3 is derived from the cloning of the NotI-KpnI fragment of AE2, containing the PCR product, into pCDNA3 (Invitrogen) digested with NotI-KpnI. It contains nucleotides 3198 to 3511 of Ad5 followed by the polyadenylation site of BGH.

The plasmid AE4 is derived from the cloning of the BglII-PvuII fragment of AE3 into pBRE1. AE4 is a plasmid containing the following E1 expression cassette:

nucleotides 1 to 3511 of Ad5, that is to say left ITR, encapsidation sequences, E1A promoter, E1A gene, E1B promoter, E1B gene the polyA of the bovine growth hormone (BGH) obtained from pCDNA3.

pBRE1 was digested with BstNI, and then digested with T4 DNA polymerase in order to fill the protruding 5' end, and then digested with XbaI. The fragment thus generated containing nucleotides 391 to 1339 of Ad5 was introduced into pic20H digested with SmaI-XbaI (nonmethylated site), to give the plasmid AE5.

The plasmid AE6 is derived from the cloning of the EcoRI-SmaI fragment of AE5 into AE4 digested with EcoRI-SmaI. AE6 is a plasmid containing the following E1 expression cassette:

nucleotides 391 to 3511 of Ad5, that is to say "reduced" promoter of E1A, E1A gene, E1B promoter, E1B gene, the polyA of the bovine growth hormone (BGH) obtained from pCDNA3.

3-2 Cloning of these two E1 cassettes into a baculovirus

The EcoRI-SphI fragments (SphI protruding 5' end which has been made blunt beforehand by digestion with T4 DNA polymerase) of the plasmids AE4 and AE6 are cloned into the plasmid pAcSG2 (Pharmingen) between the EcoRI and EcoRV sites. This generates the plasmids AE14 and AE15 respectively. In both cases, the E1 region is introduced into the locus of the polyhedrin gene (polyhedrin gene+ polyhedrin promoter being deleted).

The plasmids AE14 and 15 are cotransfected with the DNA of the baculovirus BaculoGold derived from the AcNPV strain (Pharmingen) into Sf9 insect cells, in order to generate the two corresponding recombinant baculoviruses BacAE14 and BacAE15, carrying the two cassettes for the expression of E1 integrated into the locus of the polyhedrin gene.

3-3 Cloning of a recombinant adenovirus carrying a new E1 deletion

The plasmid pCO1 (WO96/10088) was digested with BstXI, and then digested with T4 DNA polymerase in order to remove the protruding 3' end, and then digested with RsaI. The fragment thus generated containing nucleotides 3513 to 4607 of Ad5 was introduced into pBS-SK+ (Stratagene) linearized with EcoRV and then digested with calf alkaline phosphatase, to generate the plasmid AEO.

The plasmid pMA37 is obtained by ligation of the fragments:

EcoRV-NsiI of pXL2756, containing sacB. pXL2756 possesses the counter-selection gene SacB free of its EcoRI and KpnI sites, the kanamycin resistance gene, a multiple cloning site and a replication origin ColE1, NdeI-NsiI of pCO1 (containing the adeno sequences)

SalI (protruding 5' end filled with T4 DNA polymerase)-AseI of pXL2756 (kanamycin-resistant vector).

pMA37 therefore contains:

the kanamycin resistance gene the SacB gene conferring sucrose sensitivity on bacteria expressing it sequences 1 to 382 (HinfI) of Ad5 followed by sequences 3446 to 4415 (NsiI) of Ad5; there is no transgene.

The plasmid AE11 was constructed by introducing the XhoI-NsiI fragment of AEO into pMA37 digested with SalI-NSiI. It thus contains:

the kanamycin resistance gene the SacB gene conferring sucrose sensitivity on bacteria expressing it, sequences 1 to 382 (HinfI) of Ad5 followed by sequences 3513 to 4415 (NsiI) of Ad5; there is no transgene.

From the plasmid AE11 are then constructed the suicide shuttle vectors (by insertion of the transgene of interest) allowing the construction of recombinant adenoviruses by recombination in *E. Coli*. AE11 contains no sequence homologous with the plasmid AE6. The plasmids AE11 and AE4 have in common sequences 1 to 382 (HinfI) of Ad5 upstream of E1A, but there is no homology downstream of the E1 cassette between these two plasmids. Thus, there can be no generation of RCA by homologous recombination between an adeno carrying the E1 deletion existing in AE11 (that is to say 382-3513) and the baculoviruses BacAE14 or BacAE15.

3-4 Construction of a first-generation recombinant adenovirus

In the first instance, a stock of BacAE14 or is prepared according to conventional techniques. Next, the competent cells (for example HuH7) are transfected with 5 μg of plasmid pXL2822 digested with PacI (the plasmid pXL2822 contains all the Ad5 deleted for E1 (382-3446 or 382-3513) and E3 (28592-30470) and carries a cassette CMV-βGal), and infected, simultaneously or otherwise, at an MOI between 10 and 1000, with BacAE14 or 15. When the cells are lysed, the transfection supernatant is harvested, and then applied onto "fresh" competent cells previously or simultaneously infected with BacAE14 or 15 (MOI 10 to 1000), so as to amplify the adenovirus Ad2822, and so on until a stock of Ad2822 is obtained. The monitoring of the amplification of Ad2822 is facilitated by the presence of lacZ in this virus. On each amplification, the supernatant is thus pseudotitrated on W162. The genome of the virus is analysed during amplifications so as to check its integrity. Finally, this strategy has the advantage of not generating RCA in the adenovirus stocks thus produced. This absence of contamination is also verified.

4. Construction of a Baculovirus Expressing the E1 and E4 Regions of the Adenovirus 4-1 Construction of the baculovirus E1,E4 (Bac.E1-E4)

The protocol used is the following: the E1 and E4 regions are cloned in reverse orientation to the locus of the polyhedrin (Ph) gene, into the shuttle vector pBacPAK8 (Clontech, USA) to give pBacE1-E4. The recombinant baculovirus is then isolated according to conventional techniques by cotransfection of pBacE1-E4 and of the DNA of the baculovirus BacPAK6 into Sf9 cells (Kitts and Possee, Biotechniques 14(5) (1993) 810). The presence of E1 and E4 in the genome of the recombinant baculoviruses is then checked by PCR using infected Sf9 cells. The transcription of E1 and E4 in the Huh7 cells infected with the purified recombinant baculovirus is analysed by RT-PCR using cytoplasmic RNAs.

For the construction of the E1-E4 baculovirus, various fragments carrying E1 may be introduced. The fragments used in this example are those described in Example 3 for the construction of the Baculovirus-E1, containing the E1 regions under the control of their own promoter (reduced E1a promoter and E1b promoter). The E4 fragments used are the following:

fragment MaeII-MscI 32720-35835 carrying the entire E4 fragment BglII-PvuII 34115-33126 carrying the frame ORF6 fragment BglII-BglII 34115-32490 carrying the frames ORF6-ORF6/7 fragment PvuII-AluI 34801-334329 carrying the frame ORF3

These fragments are placed alternatively under the control of the E4 promoter or of different promoters, particularly of the HSV-TK or CMV promoter or of the RSV-LTR.

The positions given above refer to the sequence of the wild-type Ad5 adenovirus as published and accessible on database. Although some minor variations may exist between the various adenovirus serotypes, these positions are generally transposable to other serotypes, and in particular to Ad2, Ad7, Ad12 and Ad CAV-2.

4-2 Transcomplementation of AdΔE1ΔE4-LacZ with Bac.E1-E4

The production of the adenovirus AdΔE1ΔE4-LacZ is obtained by introduction into the competent cells of the E1,E4 baculovirus prepared in Example 4-1 and of the adenoviral genome defective for E1 and E4 (see FIG. 1). The optimum conditions for the production of AdΔE1ΔE4-LacZ in the compEtent cells, by transcomplementation with the purified Bac.E1-E4, are analysed. The AdΔE1ΔE4 titre is determined as number of β-galactosidase transduction units (t.d.u.) in the W162 line and the transcomplementation efficiency obtained is compared with that of the encapsidation line IGRP2.

5. Construction of a Baculovirus Complementing the Whole of the Adenovirus Crenome Although the simultaneous expression of several proteins, which may represent up to 13 kb of sequence, from a single virus has been reported (Belyaev and Roy, NAR 21 (1993) 1219), the maximum cloning capacity of the baculovirus is not highly documented. This example now shows that it is possible to clone the adenovirus genome deleted of its encapsidation signal (Ad.Psi-) and bordered by two loxP sites [loxP-ITR-ITR to E4 -loxP] into the baculovirus. The infection of competent cells expressing the recombinase Cre, in an inducible manner or otherwise (Cre or Cre-ER line, see Example 7), with this recombinant baculovirus and the activation of the recombinase Cre, allow the excision and the circularization of the adenoviral genome. The latter is then capable of transducing the early genes, of replicating and of activating the late genes, but incapable of being encapsidated, and thus serves as helper for the production of a minimum adenovirus (see FIGS. 2–4). In this system, the production of the minimum adenoviruses is based on the co-infection by two baculoviruses and the realization of 2 recombination events between the loxP sites. This approach has the advantage of not generating adenoviral particles from the helper virus.

The construction of the Ad.Psi- genome is carried out in *E. coli*. For that, the complete genome of the Ad5 adenovirus is cloned into a prokaryotic cloning vector, ITRs attached. The Psi sequence is deleted by enzymatic cleavage and ligation, or by site-directed mutagenesis. A LoxP sequence is then introduced on either side of the adenoviral genome, in parallel orientation. The resulting construct [loxP-ITR-ITR,ΔPsi to E4 -loxP] is then cloned into a shuttle vector allowing recombination with a baculovirus, according to the strategy described in Example 3. The recombinant baculovirus obtained, called BacAd.Psi-, is then isolated according to conventional methods.

6. Construction of a Baculovirus Comprising the Genome of the Defective Recombinant Adenovirus in Excisable Form This example describes the construction of a baculovirus which makes it possible to provide in the competent cells the genome of the defective recombinant adenovirus. More particularly, the recombinant adenovirus is defective for the whole of the coding regions, and retains only the ITR and Psi regions (minimum adenovirus, or AdΔ).

6-1 Construction of a minigenome (AdΔ) in *E. Coli*

A plasmid p[loxP-(ITR-ITR-Psi-P.CMV-LacZ-pA)-loxP] is constructed. For that, a copy of the ITR sequence of the adenovirus is isolated by enzymatic cleavage and/or amplified by PCR, and then cloned upstream of the ITR-Psi sequence contained in the shuttle vector of the adenovirus pGY63. This vector is derived from pCO1 (WO96/10088) and possesses the LacZ gene under the control of the immediate-early promoter of the cytomegalovirus (P.CMV) ending with the polyadenylation signal of the SV40 virus (pA), cloned between the ITR-Psi sequence and the gene encoding pIX. The region (ITR-ITR-Psi-P.CMV-LacZ-pA) of this vector (corresponding to a minimum adenovirus genome) is then isolated by enzymatic cleavage and cloned between the LoxP sites into the multiple cloning site of the plasmid pBS246 (Gibco), to generate the plasmid p[loxP-(ITR-ITR-Psi-P.CMV-LacZ-pA)-loxP]. The capacity to produce adEnovirus minigenomes from a circular DNA and to encapsidate them is then tested by transfection of this plasmid into the IGRP2 line infected with Ad.ΔE1ΔE4 expressing the recombinase Cre (AdCre). The minimum adenoviruses are amplified by a few successive passages of the supernatant from the transfection in the IGRP2 line. They are then purified by isopycnic caesium chloride gradient centrifugation and quantified by pseudotitration in the W162 line. It is understood that the LacZ gene can be easily replaced by any other nucleic acid of interest, by conventional molecular biology techniques.

6.2 Cloning of an excisable minigenome into a baculovirus

The construct carrying the minigenome AdΔ bordered by the two loxP sites described above is cloned at the P10 locus of the baculovirus into the shuttle vector pAcUW1 (Pharmingen, USA). The baculovirus Bac.AdΔ is then produced and isolated by conventional techniques of cotransfection into the abovementioned Sf9 cells, and selected by its phage phenotype (white), after staining with X-Gal. This baculovirus therefore carries a highly defective adenoviral genome, flanked by two loxP regions in direct orientation.

6-3 Production of AdΔ by transcomplementation with the baculovirus BacAdPsi-

Competent cells are simultaneously co-infected with the baculovirus BacAdPsi- (described in Example 5), carrying the transcomplementation functions of the whole of the adenoviral genome, and with the baculovirus Bac.AdΔ carrying the genome of the PseudoAdenovirus (described above). The recombinase Cre is provided either by adding the protein into the culture medium, or by transfecting the cells with a plasmid or a virus (baculovirus) expressing Cre, or by expression of a cassettee stably integrated into the genome of the line (as described in Example 7). The minimum adenovirus is amplified by successive passages of the culture supernatants of cells co-infected with BacAd.Psi- and with the supernatant, and then purified and titrated according to the techniques mentioned above. This technique makes it possible to obtain AdΔ as sole virus, which allows its isolation and its purification by conventional techniques. In addition, the titres obtained are compatible with an industrial use.

7. Construction of a Line Expressing the Cre Protein

A line expressing Cre, in an inducible manner or otherwise, is constructed in order to increase the efficiency of recombination between the loxP sites in the baculovirus of the invention (for example Bac.AdΔ and BacAd.Psi-) and to control the expression of Cre. In this construct, Cre is expressed alone or in the form of a C-terminal fusion protein with the oestradiol receptor (ER) binding domain (Metzger et al., 1996, cited above), under the control of a ubiquitous promoter, preferably a strong promoter inducible or otherwise. More particularly, the promoters used are the pGRE5 promoter, the metallothionin promoter, the SV40 promoter or the promoter of the HSV-TK gene.

To construct these Cre lines, the compEtent cells are cotransfected with two plasmids, one containing the Cre expression cassette (Cre or Cre-ER) and the other that for a selectable marker (Neo). G418-resistant clones are selected, the Cre activity in these clones is tested by transfection of the plasmid p(P.CMV-loxP-ATG-stop-pA-LoxP-LacZ). This plasmid contains the LacZ gene inactivated by introducing between the promoter (P.CMV) and the beginning of LacZ a succession of stop codons in the three reading frames and the signal for termination of transcription and the polyadenylation signal of the SV40 virus, bordered by two loxP sites. The expression of Cre in the clones, in the presence or otherwise of the inducer (oestradiol), is then revealed by the β-galactosidase activity induced by recombination between the two loxP sites. Several clones stably expressing the fusion protein Cre-ER or the protein Cre alone from the promoters and the competent cells specified below are thus selected. These clones can be used for the production of viruses according to the invention.

| Competent cell Recombinase | HSV-TK promoter | | SV40 promoter | | MMTV promoter | | GRE5 promoter | |
|---|---|---|---|---|---|---|---|---|
| | Cre | Cre-ER | Cre | Cre-ER | Cre | Cre-ER | Cre | Cre-ER |
| 293 | #1 | #7 | #13 | #19 | #25 | #31 | #37 | #43 |
| IGRP2 | #2 | #8 | #14 | #20 | #26 | #32 | #38 | #44 |
| Huf7 | #3 | #9 | #15 | #21 | #27 | #33 | #39 | #45 |
| HepG2 | #4 | #10 | #16 | #22 | #28 | #34 | #40 | #46 |
| HER | #5 | #11 | #17 | #23 | #29 | #35 | #41 | #47 |
| Vero | #6 | #12 | #18 | #24 | #30 | #36 | #42 | #48 |

What is claimed is:

1. A process for producing a defective recombinant adenovirus, the process comprising introducing into a competent cell a genome of a defective recombinant adenovirus and a baculovirus comprising a function necessary for transcomplementation of the defective adenoviral genome, wherein the defective recombinant adenoviral genome is introduced into the competent cell by transfection.

2. The process according to claim 1, wherein the defective recombinant adenoviral genome is introduced into the competent cell by infection.

3. The process according to claim 3, wherein the defective recombinant adenoviral genome is introduced into the competent cell using a recombinant baculovirus.

4. A process for producing a defective recombinant virus, the process comprising introducing into a competent cell a genome of a defective recombinant virus and a baculovirus comprising one or more of the functions necessary for transcomplementation of the genome, wherein the virus is a defective recombinant adenovirus.

5. The process according to claim 4, wherein the genome of the recombinant adenovirus is defective for one or more functions selected from E1, E2, E3, E4, L1–L5, pIX, and IVa2; wherein the baculovirus comprises one or more of the functions necessary for transcomplementation of the genome; and wherein the rest of the functions are provided by additional baculoviruses or by the competent cell.

6. The process according to claim 4, wherein the genome lacks any coding viral region and the baculovirus comprises all complementation functions.

7. The process according to claim 6, wherein the baculovirus comprises an entire adenoviral genome with the exception of an encapsidation region.

8. The process according to claim 6, wherein the baculovirus comprises an entire adenoviral genome with the exception of an encapsidation region and ITRs.

9. The process according to claim 4, wherein the baculovirus comprises nucleotides 391–3511 of the E1 region of Ad5 adenovirus and the genome lacks at least nucleotides 391–3511 of the E1 region.

10. The process according to claim 9, wherein the genome lacks nucleotides 383–3512 of the E1 region.

11. The process according to claim 4, wherein the competent cell is a hepatic, muscle, fibroblast, embryonic, epithelial, ocular or nerve cell.

12. The process according to claim 4, wherein the competent cell is selected from a 293 cell, a 293-derived cell comprising an additional complementation function, an A549 cell, an HuH7 cell, a Hep3B cell, a HepG2 cell, an HER cell, a 911 cell, a HeLa cell, and a KB cell.

13. A recombinant baculovirus comprising, inserted into its genome, a DNA region flanked by two nucleic acid sequences which cause site-specific recombination and which are positioned in direct orientation, wherein the DNA region comprises a replication origin functional in a competent cell and a nucleic acid encoding a complementation function of a virus, and wherein the two nucleic acid sequences which cause site-specific recombination are LoxP sequences of P1 bacteriophage.

14. A recombinant baculovirus comprising within its genome a nucleic acid encoding a complementation function of a defective virus under the control of a heterologous promoter, wherein the nucleic acid encoding the complementation function corresponds to a fragment of a canine adenovirus genome.

15. A recombinant baculovirus comprising within its genome a nucleic acid encoding a complementation function of a defective virus under the control of a heterologous promoter, wherein the complementation function is selected from the group consisting of functions encoded by adenovirus E1, E2, E4, late genes L1 to L5, pIX, and Iva2 regions, wherein the promoter comprises a promoter region naturally responsible for the expression of the complementation function.

16. The recombinant baculovirus of claim 15, wherein the promoter is a strong cellular promoter.

17. The recombinant baculovirus of claim 15, wherein the promoter is regulated.

18. The recombinant baculovirus of claim 15, wherein the complementation function comprises the E4 region of an adenoviral genome.

19. The recombinant baculovirus of claim 15, wherein the complementation function comprises the E4 ORF3 or E4 ORF6 of an adenoviral genome.

20. The recombinant baculovirus of claim 15, wherein the baculovirus comprises all the coding regions of an adenoviral genome.

21. The recombinant baculovirus of claim 15, wherein the baculovirus comprises an entire adenoviral genome except an encapsidation region.

22. The recombinant baculovirus of claim 15, wherein the nucleic acid is introduced at the baculovirus p10 locus.

23. A process for producing a defective recombinant adeno-associated virus, the process comprising introducing into a competent cell a genome of a defective recombinant adeno-associated virus and a baculovirus comprising a function necessary for transcomplementation of the defective adenoviral genome, wherein the defective recombinant adeno-associated viral genome is introduced into the competent cell by transfection.

24. The process according to claim 23, wherein the defective recombinant adeno-associated viral genome is introduced into the competent cell by infection.

25. The process according to claim 23, wherein the defective recombinant adeno-associated viral genome is introduced into the competent cell using a recombinant baculovirus.

26. The process according to claim 23, wherein the transcomplementation function is encoded by adeno-associated virus (AAV) Rep region.

27. The process according to claim 23, wherein the transcomplementation function is encoded by adeno-associated virus (AAV) Cap region.

* * * * *

UNITED STATES PATENT AND TRADEMARK OFFICE
CERTIFICATE OF CORRECTION

PATENT NO. : 6,387,670 B1  
DATED : May 14, 2002  
INVENTOR(S) : Helene Leblois-Prehaud et al.

It is certified that error appears in the above-identified patent and that said Letters Patent is hereby corrected as shown below:

<u>Column 24,</u>
Line 1, change "3" to -- 2 --.

Signed and Sealed this

Eighth Day of October, 2002

*Attest:*

*Attesting Officer*

JAMES E. ROGAN
*Director of the United States Patent and Trademark Office*